US008663178B2

United States Patent
De Luca

(10) Patent No.: US 8,663,178 B2
(45) Date of Patent: Mar. 4, 2014

(54) REINFORCED STOCKING OR SOCK FOR THE PREVENTION AND/OR TREATMENT OF HALLUX VALGUS

(76) Inventor: Carlo De Luca, Sarmeola di Rubano (IT)

(*) Notice: Subject to any disclaimer, the term of this patent is extended or adjusted under 35 U.S.C. 154(b) by 666 days.

(21) Appl. No.: 12/526,546

(22) PCT Filed: Feb. 19, 2008

(86) PCT No.: PCT/IT2008/000108
§ 371 (c)(1),
(2), (4) Date: Oct. 27, 2009

(87) PCT Pub. No.: WO2008/102405
PCT Pub. Date: Aug. 28, 2008

(65) Prior Publication Data
US 2010/0106110 A1  Apr. 29, 2010

(30) Foreign Application Priority Data

Feb. 20, 2007 (IT) .............................. PD2007A0052

(51) Int. Cl.
*A61M 35/00* (2006.01)
(52) U.S. Cl.
USPC ............................................. 604/293; 2/239
(58) Field of Classification Search
USPC ........... 2/239–241; 604/289, 293; 602/30, 48; 62/30, 48, 63, 75
See application file for complete search history.

(56) References Cited

U.S. PATENT DOCUMENTS

| 2,102,368 | A | * | 12/1937 | Martel | 66/182 |
| 3,013,564 | A | * | 12/1961 | Levey | 36/170 |
| 3,856,008 | A | * | 12/1974 | Fowler et al. | 602/62 |
| 4,856,505 | A |  | 8/1989 | Shaffer |  |
| 5,282,782 | A |  | 2/1994 | Kasahara |  |
| 5,617,745 | A | * | 4/1997 | Della Corte et al. | 66/178 A |
| 6,012,177 | A | * | 1/2000 | Cortinovis | 2/239 |
| 6,315,749 | B1 | * | 11/2001 | Sunayama | 602/23 |
| 6,673,054 | B1 | * | 1/2004 | Gould et al. | 604/292 |
| 6,708,348 | B1 | * | 3/2004 | Romay | 2/239 |
| 7,192,411 | B2 | * | 3/2007 | Gobet et al. | 602/63 |
| 2003/0005601 | A1 | * | 1/2003 | Kasahara | 36/88 |

FOREIGN PATENT DOCUMENTS

| DE | 10154185 A1 | 5/2003 |
| DE | 202006010193 U1 | 8/2006 |
| FR | 2879437 A | 6/2006 |

OTHER PUBLICATIONS

International Search Report, Jun. 26, 2008.

\* cited by examiner

*Primary Examiner* — Tatyana Zalukaeva
*Assistant Examiner* — Benedict L Hanrahan
(74) *Attorney, Agent, or Firm* — Themis Law

(57) ABSTRACT

A stocking or sock with a foot portion includes a pocket for containing the big toe that is separate from the pocket(s) for the other toes. At least one medial reinforcement, integrally attached to the foot portion, entirely or partially surrounds the big toe pocket, while the medial part of the foot portion, and the posterior part or heel of the foot portion are anchored to the posterolateral or lateral part of foot portion, coming to bear on the anterior part of said pocket, counteracting any lateral deflections, and on the medial part, corresponding to the metatarsophalangeal joint and the first metatarsal of the foot, counteracting any medial deflections.

15 Claims, 5 Drawing Sheets

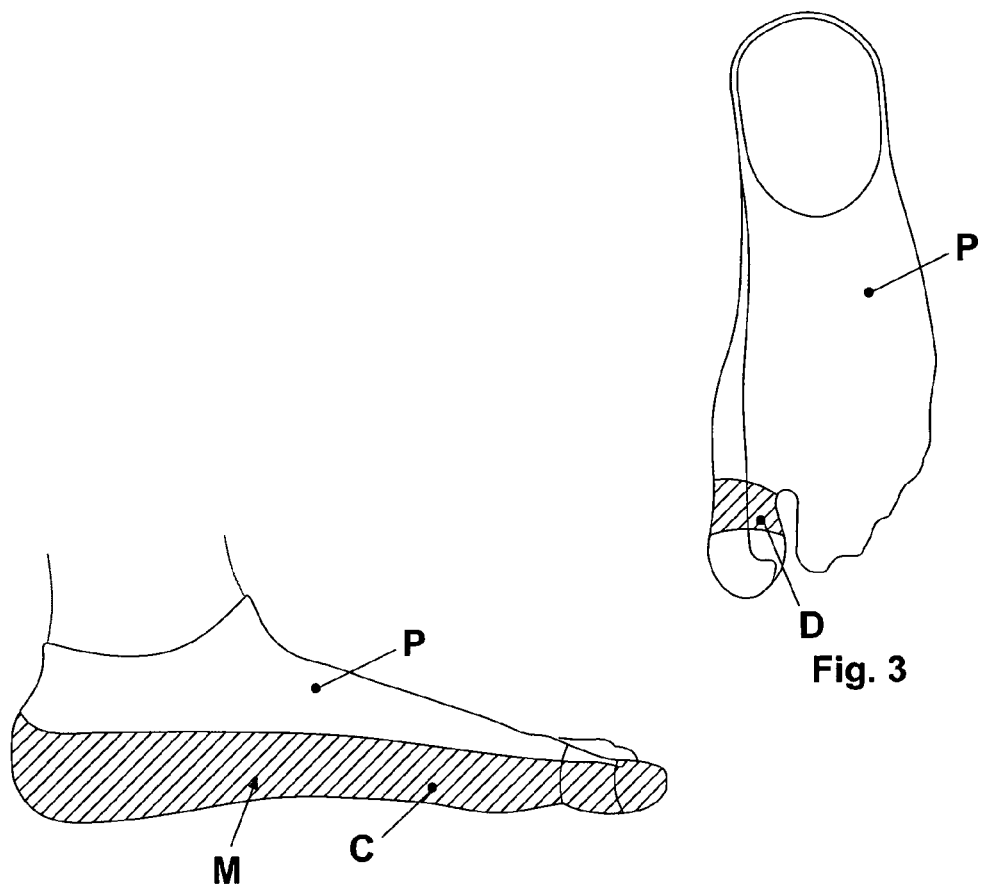
Fig. 3
Fig. 4
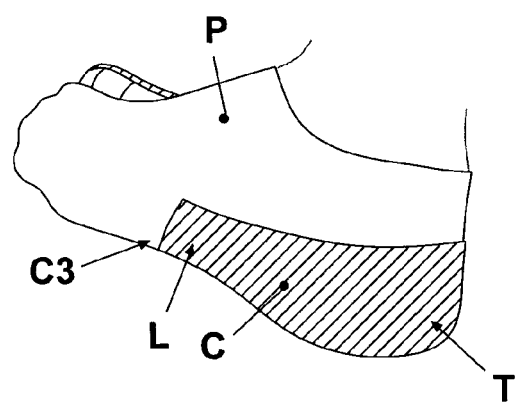
Fig. 5

REINFORCED STOCKING OR SOCK FOR THE PREVENTION AND/OR TREATMENT OF HALLUX VALGUS

FIELD OF THE INVENTION

The present invention relates to a new stocking or sock with reinforcement designed to be suitable for maintaining the natural mutual osteoarticular arrangement of the parts of the foot. The present invention is useful in the prevention and/or treatment of hallux valgus.

BACKGROUND OF THE INVENTION

Hallux valgus is a well-known foot disorder, commonly called bunions, consisting in the lateral deflection of the big toe (or hallux), with a medial deflection of the first metatarsal and the risk of sublimation of the metatarsophalangeal joint of the first radius of the foot.

This disorder consists substantially in the end of the first metatarsal moving away from the other toes and the foot consequently becoming splayed, giving rise to the characteristic protuberance on a level with the metatarsophalangeal joint.

Due to this splaying effect, the base on which the hallux rests is displaced, making the toe deflect outwards.

The first metatarsal and the big toe are consequently no longer aligned but form an angle between them, leading to localized foot disorders and also having repercussions on the entire body's postural alignment.

In fact, when the metatarsophalangeal joint becomes misaligned, it functions asymmetrically, leading to wear on the cartilage components and also causing inflammation that induces further degeneration and pain for the patient. Patients suffering from this disorder cannot wear normal shoes because their bunion impacts against the shoe, leading to troublesome episodes of bursitis.

The lateral deflection of the hallux also gives rise to a bending of the other toes and the progressive subluxation of the joint, even progressing to complete luxation.

Further consequences of hallux valgus include postural misalignments and defects, particularly affecting the knee, the hips and the lumbar part of the spinal column.

There are numerous known surgical techniques for the treatment of hallux valgus, designed mainly to realign the joint of the first radius by means of a lateral translation of the end of the first metatarsal.

The majority of the surgical procedures for treating hallux valgus are extremely invasive and invalidating, with unpleasant consequences and discomfort for the patient during the postoperative course.

Functional restraining dressings are also well known and are often used in the prevention and/or postoperative treatment of hallux valgus disorders.

Functional dressings are a type of bandage that assures only a partial immobilization: they do not prevent the movement of the joints, but they do counteract the forces that can give rise to unwanted deflections.

The therapeutic effectiveness of functional dressings depends mainly on their proper application, using particular techniques that can be handled only by qualified personnel, whereas the patient is usually unable to apply them alone.

Even if a patient could rely on the use of pre-shaped dressings, their application would be particularly complex, especially for elderly people and those with a limited mobility.

SUMMARY OF THE INVENTION

The object of the present invention is a new elastic or inelastic, pre-shaped and reinforced stocking or sock for the prevention and/or containment and/or treatment of various stages of the disorder commonly called hallux valgus.

The main object of the present invention is to provide users with a device that is immediately and easily applicable, and capable of counteracting the pathological deflections characteristic of the condition called hallux valgus.

Another important object of the present invention is particularly to counteract the misalignment of the first radius of the foot, while also protecting the metatarsophalangeal joint against luxation and trauma.

Another important object of the present invention is to restrict any splaying of the forefoot, counteracting the separation of the metatarsal bones, thereby contributing to the adoption of a correct posture.

Another object of the present invention is to exert differential pressures on the foot, facilitating the natural "pumping effect", as well as performing a massage on the medial musculature of the foot.

An important advantage of the present invention stems from the fact that the novel stocking or sock can be worn just like a normal sock, without the practical complications of functional restraining dressings and consequently without the need for action by qualified personnel.

Another important advantage of the present invention consists in that it does not cause any motion impediment or discomfort for the user, who can wear the sock at any time, even while wearing normal shoes.

Another important advantage of the present invention consists in that it the novel stocking or sock may be pre-packaged in various sizes and consequently made available to users just like a normal stocking or sock.

These and other, direct and complementary objects are achieved by the new pre-shaped and reinforced elastic stocking or sock for the prevention, containment and/or treatment of hallux valgus, which comprises a foot portion suitable for covering all or part of the patient's foot, and possibly also a leg portion of any height, suitable for covering the ankle and/or part of the leg.

The anterior part of the foot portion, i.e. the part surrounding the toes, comprises a pocket for the first or big toe that is separate from the pocket for the other toes.

The sock comprises one or more additional reinforcements applied to said foot portion and coming to bear particularly on the medial part of the foot, the principal purpose of which is to contain or obstruct any lateral deflections of the big toe and medial deflection of the first metatarsal.

Said reinforcements comprise one or more localized areas or bands made of synthetic and/or natural, elastic and/or inelastic fibers, wherein the elasticity of said bands depends on the characteristic elasticity of the fibers used, the gauge of the yarn, and/or the particular combination of fibers used.

For instance, said fibers may be made of an elastomeric or other suitable material.

According to a first embodiment of the invention, said bands comprise one or more strips of elastic and/or inelastic material generically applied to the foot portion, e.g. by means of stitching, adhesives, and/or other procedures designed to ensure their integral attachment to the foot portion of the sock.

According to a possible further embodiment, said bands are directly woven into the fabric of the foot portion, i.e. they comprise a plurality of synthetic and/or natural, elastic and/or inelastic fibers woven into the fabric of the foot portion and arranged along lines of force designed particularly to bear with a containing action on the metatarsophalangeal joint of the first tarsus.

More in detail, the new stocking or sock comprises at least one first reinforcement, hereinafter called the medial reinforcement, anchored to said pocket for containing the big toe and covering at least the medial face of the foot portion of the sock, extending at least from the base of the hallux, just above the metatarsophalangeal joint, to at least the anteromedial third of the tarsus.

For instance, said band may extend so as to entirely or partially surround the posterior part or heel, or even to the lateral face of the foot portion of the sock, being stably anchored thereto.

When the new sock is worn, said medial reinforcement anchors the big toe inserted in the pocket and applies thereon a force that tends to deflect the toe medially, thus counteracting the pathological tendency of the hallux valgus to deflect laterally.

Said medial reinforcement also opposes the medial deflection of the first metatarsal, containing it and exerting on it a force in the opposite, lateral direction.

Basically, said medial reinforcement serves the purpose of containing and counteracting the misalignment between the phalanx and the first metatarsal, while also reinforcing the ligament capsule of the metatarsophalangeal joint of the first radius of the foot, helping to prevent its subluxation.

A further function of the medial reinforcement is to protect the metatarsophalangeal region of the first radius against trauma of various kinds, also and above all with a view to preventing the onset of bursitis.

In addition to said medial reinforcement, the new sock may also comprise an additional reinforcement, or hallux reinforcement, consisting substantially of a band wrapping as a complete or partial ring around said pocket for the big toe, over its anterior part at least, or covering the full length of the pocket.

The purpose of said hallux reinforcement is substantially to enable a greater anchorage of said medial reinforcement, thereby helping to separate the big toe from the second toe, moving the big toe further away in a medial direction.

According to a further embodiment of the invention, the new sock comprises another reinforcement, hereinafter called the anterior transversal reinforcement, which entirely or partially surrounds the anterior part of the foot portion of the sock. In particular, said anterior transversal reinforcement wraps around the medial face at least of the anterior part of the foot portion, coinciding with the forefoot, on a level with the metatarsophalangeal joint. Said anterior transversal reinforcement can also totally or partially surround the anterior dorsal face of the foot portion and the ventral face of the foot portion.

Alternatively, said anterior transversal reinforcement may wrap entirely in a ring around the anterior part of the foot portion.

The main purpose of the anterior transversal reinforcement is to operate, in synergy with said medial reinforcement, particularly to counteract the medial deflection of the metatarsal of the first radius of the foot, thereby containing the subluxation of the metatarsophalangeal joint of the big toe.

Said anterior transversal reinforcement also keeps said medial reinforcement in the right position, facilitating the proper positioning of the sock on the patient's foot.

Said anterior transversal reinforcement and said medial reinforcement also serve the purpose of strengthening and containing the medial musculature of the foot.

In addition or as an alternative to said anterior transversal reinforcement, the new sock may also comprise a posterior transversal reinforcement that wraps completely in a ring patterns around the foot portion on a level with the proximomedial third of the tarsus.

Like the complete or partial anterior transversal reinforcement, said posterior transversal reinforcement helps in guiding the proper positioning of the sock on the foot, since it controls and maintains the position of the medial reinforcement.

The posterior transversal reinforcement also serves the purpose of counteracting any medial deflection of the first radius of the foot, preventing the tendency of the forefoot to become splayed, while also exerting an elastic restraining action on the musculature of the foot and consequently having a massage effect.

The new reinforced sock may comprise both of said anterior and posterior reinforcements, in which case said anterior reinforcement is designed to be more taut than said posterior reinforcement, so that they exert differential pressures on the foot; in particular, the anterior reinforcement exerts a greater pressure than the posterior reinforcement in order to stimulate the foot during the stepping action, facilitating the so-called "pumping effect" and massaging the medial musculature of the foot.

In fact, the application of a gradually greater pressure on the more distal parts of the foot by comparison with the proximal parts, together with the medial displacement of the hallux, which is accentuated due to the effect of the bands during the stepping action, also has a more powerful lymph-draining effect than support socks or dressings.

According to a further embodiment, said anterior and posterior transversal reinforcements are combined together into a single wider reinforcement wrapping in a ring around the foot portion on a level with the metatarsophalangeal joint and the proximomedial third of the tarsus. Said all-in-one transversal reinforcement has a differential elasticity so as to exert differential pressures, as explained above, along the foot.

The new sock can also be designed to comprise one or more further oblique reinforcements coming to bear with forces directed not in the crosswise direction (as in the case of the above-mentioned transversal reinforcements), but obliquely, in a craniocaudal/lateromedial direction, and arranged at least over the dorsal part of the foot portion of the sock, particularly on a level with the metatarsophalangeal joint.

Moreover, these oblique reinforcements are also designed to exert differential pressures on the foot that decrease from the distal area of the foot towards the proximal area of the foot, to facilitate the lymph-draining action.

To prevent the sum of the actions of said transversal reinforcements (coming to bear with forces in a lateromedial direction) and said oblique reinforcements (coming to bear with forces in a craniocaudal/lateromedial direction) from producing a resultant force on the big toe that would cause its deflection in a non-lateromedial direction, said pocket for the big toe is shaped in a particular manner, for example, using one or more of the following methods.

In particular, said pocket for the big toe may comprise a lateral face, i.e. facing towards the pocket for the other toes, that is longer than its medial face.

The two pockets for the toes, i.e. the pocket for the big toe and the pocket for the remaining toes, can be set at a distance of a few millimeters from one another and arranged so as to form an acute angle different from zero with respect to one another.

In this way, when the big toe is inserted correctly inside its pocket in the foot portion of the sock, it must occupy a position, in which it is separated in the medial direction from the other toes, so that the resultant of the forces brought to bear by said reinforcements comes to bear on the big toe, preventing it from deflecting laterally and forcing it instead to deflect in the medial direction.

The new sock is pre-shaped and ready to wear, since the reinforcements are stably attached to or woven directly into the fabric of the foot portion, so that they constantly remain in the right position to enable them to have the right effect on the foot.

The new sock can consequently be worn just like a normal stocking or sock, without having to take any action on the reinforcements and thus overcoming the problem of the complexity in application of functional restraining dressings, which need to be applied by qualified personnel.

The user of the new sock can wear normal footwear, since the sock is of limited thickness and does not interfere with the normal mobility of the foot; moreover, it protects the metatarsophalangeal joint against friction with the footwear being worn.

In particular, the new sock is extremely useful in cases of limited deformity because it counteracts any progression of the deflections; it can also provide relief in the case of painful syndromes since it also helps in protecting the metatarsophalangeal joint of the first radius of the foot.

The new sock also provides a firm grip on the central part of the foot, preventing any splaying of the radii (i.e. medial and lateral deflections of the metatarsals) and rebalancing the loads on the foot during stepping, with a consequent positive effect on the person's general posture.

Moreover, the new stocking or sock can be made of a sterilized and antiseptic material to guarantee the best conditions of hygiene. For instance, the new sock can include silver fibers in the preparation of the fabric used for the sock, the silver fibers being known for their effectiveness as antimicrobial agents. The sock can also be treated with antiseptics using specific, dedicated substances.

BRIEF DESCRIPTION OF THE DRAWINGS

The characteristics of the present invention will become more apparent from the following description with reference to the drawings, which are attached herein to illustrate a non-limiting example.

FIG. 3 shows the dorsal part of the new sock (N), in particular with the hallux reinforcement (D) integrally attached to the foot portion (P).

FIGS. 4 and 5 respectively show the medial face (M) and the posterolateral face (L) of the sock, with the position of the medial reinforcement (C) integrally attached to the foot portion (P).

DETAILED DESCRIPTION OF THE INVENTION

Referring to the figures, the new pre-shaped stocking or sock (N), made of elastic or inelastic material, comprises a foot portion (P) with a pocket (A) for the big toe that is separate from the pocket (B) for the other toes.

Figure 13:
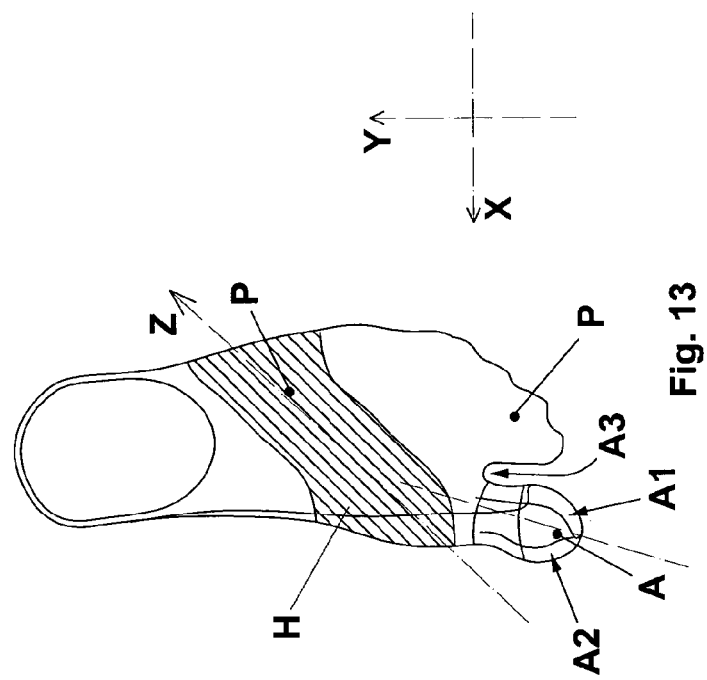
FIG. 13 shows the dorsal part of the new sock (N), with the oblique reinforcements (H) arranged on a slant with respect to said medial reinforcement (C) in the craniocaudal/lateromedial direction (Z). This figure also shows a particular possible shaping and arrangement of the pocket (A) for the big toe in relation to the pocket (B) for the second toe.

According to the illustration in FIG. 13, said pocket (A) for the big toe clearly comprises a lateral face (A1), facing towards the pocket (B) for the other toes, that is longer than its medial face (A2).

Moreover, as an alternative or in combination with the previous feature, said pocket (A) for the big toe and said pocket (B) for the remaining toes are separated from one another (A3) by a few millimeters and arranged so as to form an acute angle different from zero with respect to one another, said pocket (A) for the big toe being slightly slanting with respect to the craniocaudal direction (Y), in the distolateral direction (X).

Figure 1:
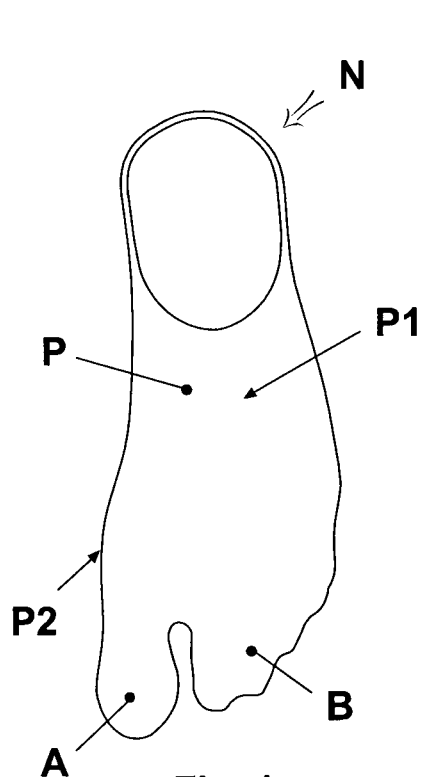
FIG. 1 shows the dorsal part of the sock (N), where the foot portion (P) comprises at least one pocket (A) for the big toe that is separate from the pocket(s) (B) for the other toes.
Figure 2A:
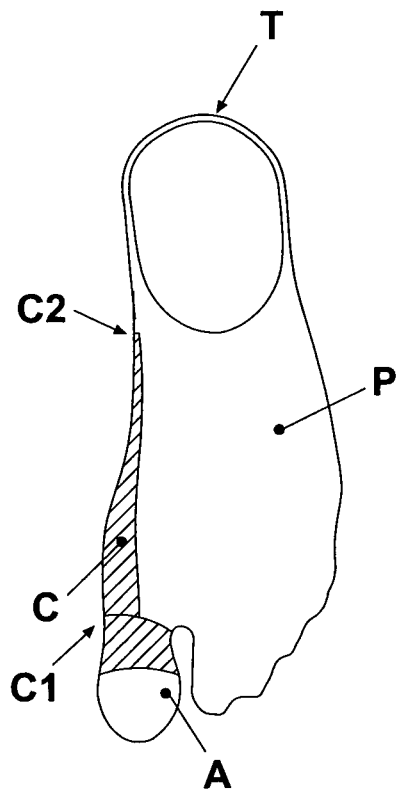
FIGS. 2a and 2b show the dorsal part of the new sock (N), with only the medial reinforcement (C) integrally attached to the foot portion (P) according to two possible embodiments.

As shown in FIG. 2a, the new sock (N) comprises at least one medial reinforcement (C) anchored to said pocket (A) for the big toe and affecting the medial face (M) of the foot portion of the sock, from at least one point (C1) at the base of the pocket (A) up to at least one point (C2) corresponding to the anteromedial third of the tarsal region.

Said medial reinforcement (C) can also extend to surround the whole or part of the heel (T), or to an intermediate point (C3) on the lateral face (L) of the foot portion (P), as shown in FIG. 5.

Figure 2B:
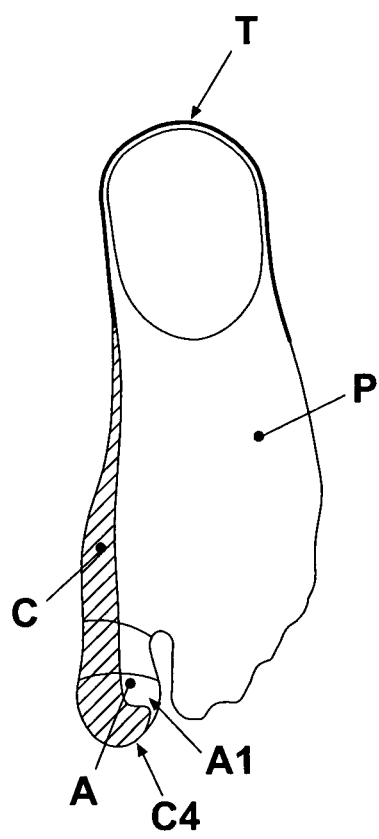

Alternatively, said reinforcement (L) can also be anchored to a point (C4) on the lateral face (A1) of said pocket (A) for the big toe so as to wrap entirely or partially around said pocket (A), as shown in FIG. 2b.

Said medial reinforcement (C) brings a force to bear on the big toe inserted in the corresponding pocket (A) in a mediolateral direction (X), while it takes effect in the lateromedial direction (i.e. in the opposite direction) on the medial face of the foot, coinciding with the metatarsophalangeal joint (P2).

The new sock (N) may also comprise a further hallux reinforcement (D), consisting substantially of a band wrapping in a full or partial ring around said pocket (A) for the big toe.

Figure 6:
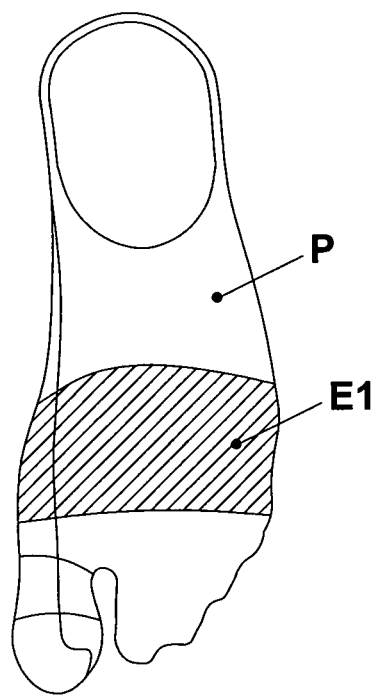
FIGS. 6 and 7 show the dorsal part of the new sock (N), with the medial (C), the hallux (D) and the anterior transversal (E1, E2) reinforcements, with the latter respectively in the complete (E1), i.e. forming a ring around the foot portion (P), and partial (E2) versions.

In the further possible embodiment shown in FIG. 6, the new sock (N) comprises an anterior transversal reinforcement (E1) that entirely surrounds the front of the foot portion (P) corresponding to the forefoot, on a level with the metatarsophalangeal joint (P2).

Figure 7:
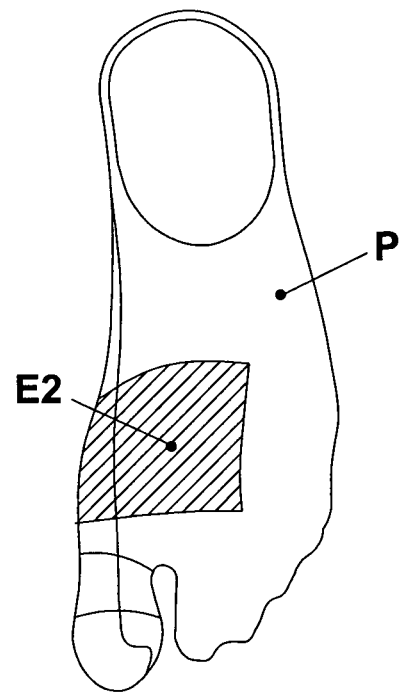

In the possible embodiment shown in FIG. 7, said anterior transversal reinforcement (E2) partially surrounds the foot portion (P), covering at least part of the medial face (M) on a level with the metatarsophalangeal joint (P2).

Figure 8:
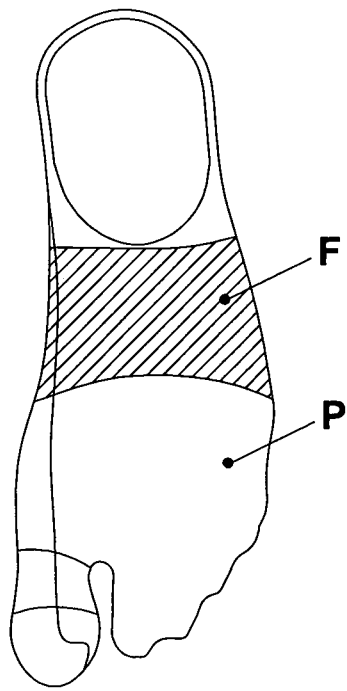
FIG. 8 shows the dorsal part of the new sock (N), with the medial (C), the hallux (D) and the full posterior transversal (F) reinforcements.

In the possible embodiment shown in FIG. 8, moreover, as an alternative to said anterior transversal reinforcement (E1) or (E2), the new sock (N) comprises a posterior transversal reinforcement (F), forming a ring completely surrounding the foot portion (P) on a level with the proximomedial third of the tarsus (P1).

Figure 9:
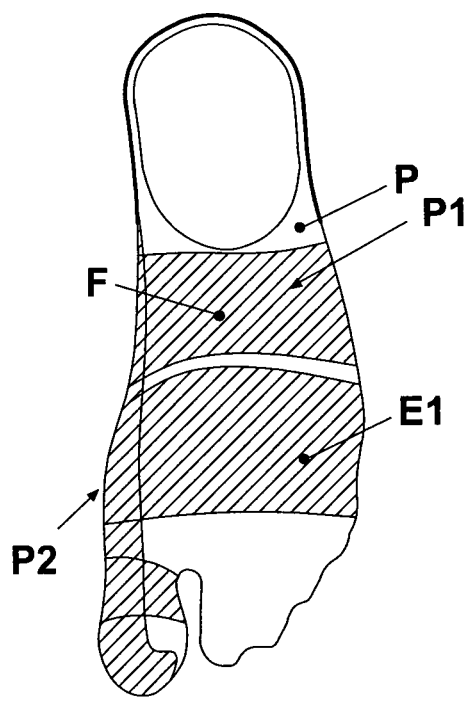
FIGS. 9 and 10 show the dorsal part of the new sock (N), with the medial (C), the hallux (D) and the full posterior transversal (F) and anterior transversal (E1, E2) reinforcements, the latter respectively in the complete (E1) and partial (E2) versions.
Figure 10:
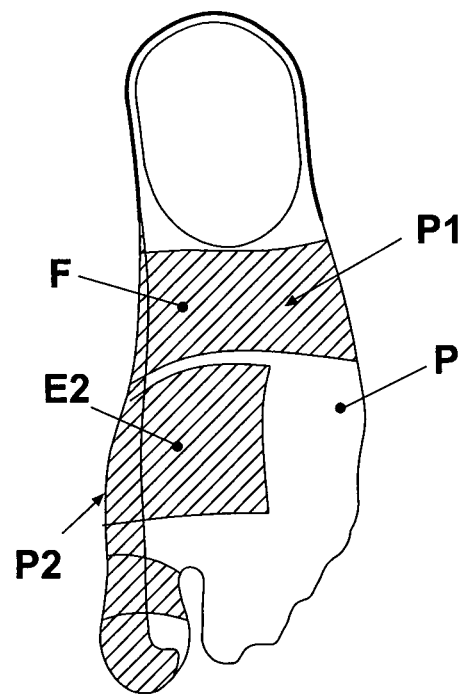
Figure 11:
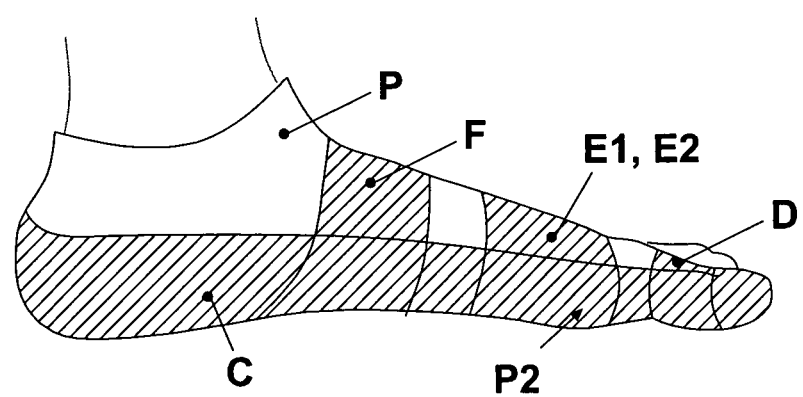
FIG. 11 shows a medial view.
Figure 12:
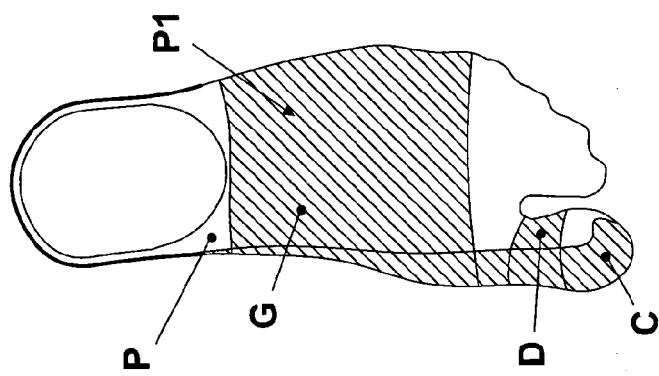
FIG. 12 shows the dorsal part of the new sock (N), with the medial (C), the hallux (D) and the all-in-one transversal (G) reinforcements, the latter forming a ring surrounding the foot portion (P), on a level with the proximomedial third of the tarsus (P1) and the metatarsophalangeal joint (P2).

The new reinforced sock (N) may also comprise one or more, or both of said anterior (E1, E2) and posterior (F) reinforcements, as shown in FIGS. 9 and 10, or said anterior and posterior transversal reinforcements may be combined into a single, wider reinforcement (G), as shown in FIG. 12, forming a ring surrounding the foot portion (P) on a level with the metatarsophalangeal joint (P2) and the proximomedial third of the tarsus (P1).

In the solution shown in FIG. 13, as an alternative or in combination with one or more of said anterior transversal (E1, E2) or posterior (F) or wider (G) reinforcements, the new sock (N) may also comprise one or more oblique reinforcements (H), designed to cover at least the dorsal part of the foot portion (P), particularly on a level with the metatarsophalangeal joint (P2), and arranged in a slanting position with respect to said medial reinforcement (C), i.e. in a craniocaudal/lateromedial direction (Z).

Thus, with reference to the above description and to the content of the illustrations, the following claims are submitted.

What is claimed is:

1. An elastic or inelastic stocking or sock comprising:
   a foot portion suitable for covering at least part of a foot, the foot portion comprising,
     a pocket configured to contain the big toe (hallux);
     one or more pockets configured to contain the other toes, the one or more pockets for the other toes being separate from the pocket for the big toe;
     at least one medial reinforcement comprising an area or band integrally attached to the foot portion and surrounding a medial part of the foot portion from at least one point at a base of said pocket for the big toe, to at least one other point corresponding to heel region;
     at least one big toe reinforcement integrally attached to said foot portion and surrounding said pocket for the big toe, said medial reinforcement being anchored to said big toe reinforcement, said big toe reinforcement pulling the big toe outwardly, wherein said medial reinforcement comes to bear:
       on said pocket the big toe, thereby counteracting any lateral deflections; and
       on the medial part of the stocking or sock corresponding to the metatarsophalangeal joint and on the first metatarsal of the foot, thereby counteracting any medial deflections;
     at least one anterior transversal reinforcement comprising at least one band integrally attached to the foot portion and surrounding and covering an anterior part of foot portion on a level with the metatarsophalangeal joint, wherein said anterior transversal reinforcement comes to bear the medial reinforcement; and
     at least one posterior transversal reinforcement comprising at least one band integrally attached to the foot portion and forming a ring surrounding the heel, on a level with the proximomedial third of the tarsus, the posterior transversal reinforcement further coming to bear on the medial reinforcement.

2. The stocking or sock according to claim 1, wherein said medial reinforcement, anterior transversal reinforcement and posterior transversal reinforcement are integral with said big toe reinforcement.

3. The stocking or sock according to claim 1, wherein the pocket for containing the big toe is configured to contain only the big toe, separate from the one or more pockets for the remaining toes, wherein the at least one medial reinforcement comprises the area or band integrally attached to said foot portion, the area or band entirely or partially surrounding said pocket for the big toe, the medial part of the foot portion and a posterior part comprising the heel of the foot portion being anchored to the posterolateral or lateral part of the foot portion.

4. The stocking or sock according to claim 1, wherein said anterior transversal reinforcement forms a ring completely surrounding the foot portion, on a level with the metatarsophalangeal joint and the metatarsal of the first radius of the foot.

5. The stocking or sock according to claim 1, wherein said anterior transversal reinforcement surrounds at least a part of a medial face, a dorsal face and a ventral face of the foot portion, on a level with the metatarsophalangeal joint and the metatarsal of the first radius of the foot.

6. The stocking or sock according to claim 1, wherein the posterior transversal reinforcement forms a ring surrounding and covering the foot portion.

7. The stocking or sock according to claim 1, wherein said anterior transversal reinforcement has a greater elastic tension than said posterior transversal reinforcement.

8. The stocking or sock according to claim 1, further comprising a posterior transversal reinforcement with a band integrally attached to said foot portion and forming a ring surrounding and covering the foot portion posteriously of the anterior transversal reinforcement.

9. The stocking or sock according to claim 1, further comprising at least one oblique reinforcement with at least one band integrally attached to said foot portion and covering at least a dorsal part of the foot portion on a level with the metatarsophalangeal joint, the oblique reinforcement being arranged in a craniocaudal/lateromedial direction.

10. The stocking or sock according to claim 9, wherein said oblique reinforcement surrounds said foot portion, coming to bear with a differential pressure that decreases from a distal area of the foot portion toward a proximal area of the foot portion.

11. The stocking or sock according to claim 1, wherein said pocket for the big toe comprises lateral face longer than a medial face, and wherein said pocket for the big toe is separated, at a base, from said pocket for the other toes, and is on a slant with respect to a craniocaudal direction toward a mediolateral direction.

12. The stocking or sock according to claim 1, wherein one or more of the medial reinforcement or any other reinforcements comprise one or more strips of synthetic, natural, elastic, or inelastic fibers, which are stitched, glued, or otherwise attached to said foot portion, so as to adhere thereto and form an integral part of the foot portion.

13. The stocking or sock according to claim 12, wherein the one or more of said medial reinforcements or any other reinforcements is made of the synthetic, natural, elastic, or inelastic fibers woven directly into a fabric of said foot portion and arranged along lines of force that exert an action to contain any deflections of the metatarsophalangeal joint of the first radius of the foot.

14. The stocking or sock according to claim 1, wherein the stocking or sock is made entirely or partially of an antiseptic material and/or is submitted to an antiseptic treatment.

15. The stocking or sock according to claim 1, further comprising a transversal reinforcements comprising a plurality of bands integrally attached to said foot portion and forming rings surrounding and covering the foot portion on a level with the metatarsophalangeal joint and on a level with the proximomedial third of the tarsus, wherein a band disposed a closer to the big toe has an elastic tension greater than another band disposed further away from the big toe.

* * * * *